(12) United States Patent
Fisher et al.

(10) Patent No.: US 9,119,686 B2
(45) Date of Patent: Sep. 1, 2015

(54) ORAL ORTHOSIS HANDLE

(75) Inventors: Jeffrey Joe Fisher, Ada, MI (US); Scott Salmon, Tenafly, NJ (US); Josh Hartl, Bloomfield, NJ (US)

(73) Assignee: Ranir, LLC, Grand Rapids, MI (US)

( * ) Notice: Subject to any disclaimer, the term of this patent is extended or adjusted under 35 U.S.C. 154(b) by 775 days.

(21) Appl. No.: 13/302,295

(22) Filed: Nov. 22, 2011

(65) Prior Publication Data

US 2013/0130193 A1    May 23, 2013

(51) Int. Cl.
| | |
|---|---|
| A61F 5/56 | (2006.01) |
| A61F 11/00 | (2006.01) |
| A61B 19/02 | (2006.01) |
| A61C 9/00 | (2006.01) |
| A61F 5/00 | (2006.01) |
| A61C 8/00 | (2006.01) |
| A61C 7/00 | (2006.01) |
| A61C 19/00 | (2006.01) |
| A61C 7/08 | (2006.01) |
| A61C 19/02 | (2006.01) |
| A61C 3/00 | (2006.01) |
| A61C 5/14 | (2006.01) |

(52) U.S. Cl.
CPC .................. *A61C 9/0006* (2013.01); *A61C 7/00* (2013.01); *A61C 7/08* (2013.01); *A61C 8/00* (2013.01); *A61C 8/0087* (2013.01); *A61C 19/00* (2013.01); *A61C 19/02* (2013.01); *A61F 5/00* (2013.01); *A61F 5/56* (2013.01)

(58) Field of Classification Search
CPC .......... A61C 7/08; A61C 8/00; A61C 8/0087; A61C 19/00; A61C 19/02; A61F 5/00; A61F 5/56
USPC ............ 128/848, 857, 859–862; 433/6, 7, 34, 433/35, 49, 71, 82, 85, 45–46; 206/63.5
See application file for complete search history.

(56) References Cited

U.S. PATENT DOCUMENTS

| | | | | |
|---|---|---|---|---|
| 1,127,635 | A * | 2/1915 | Kerr ................................ 433/46 |
| 3,864,832 | A * | 2/1975 | Carlson ......................... 128/862 |
| 4,401,616 | A * | 8/1983 | Wagner ......................... 264/138 |
| 4,867,680 | A * | 9/1989 | Hare et al. ..................... 433/37 |
| 5,313,960 | A * | 5/1994 | Tomasi ......................... 128/848 |
| 5,320,114 | A * | 6/1994 | Kittelsen et al. ............... 128/861 |
| 5,611,169 | A * | 3/1997 | Mayer ......................... 43/44.84 |
| 6,017,217 | A * | 1/2000 | Wittrock ........................ 433/37 |
| 6,581,603 | B1 * | 6/2003 | Schames ....................... 128/848 |
| 8,733,238 | B2 * | 5/2014 | Myoung ......................... 99/499 |
| 2011/0146015 | A1 * | 6/2011 | Moskovich et al. ......... 15/167.1 |

* cited by examiner

*Primary Examiner* — Victoria J Hicks
*Assistant Examiner* — Brandon L Jackson
(74) *Attorney, Agent, or Firm* — Price Heneveld LLP (57) ABSTRACT

A handle for removably attaching to a moldable orthosis positions the orthosis in boiling water. The handle includes an arm with an oral orthosis engaging member at one end. The engaging member includes one of a tab or slot which removably engages the oral orthosis. In a preferred embodiment, the arm further includes a hook-like member for supporting the oral orthosis on the rim of a container of boiling water during the molding process. In one embodiment, the handle forms the cover of a storage case for the orthosis.

3 Claims, 7 Drawing Sheets

ORAL ORTHOSIS HANDLE

BACKGROUND OF THE INVENTION

The present invention relates to a handle for an oral orthosis with improved molding characteristics.

Oral orthoses are typically shaped like mouthpieces which include a holder in the form of a curved tray made of a semi-rigid polymeric material, such as polycarbonate. The holder is filled with a moldable polymeric material for use by a dental professional or consumer in shaping the interior moldable content of the mouthpiece into a comfortable, tooth-conforming mouthpiece. Such orthoses are employed for in a variety of applications such as mouth guards for sporting events, bite guards to treat bruxism at night, and snore prevention devices which are designed to urge the lower jaw slightly forwardly to provide clearance between the rear of the tongue and the uvula, which is the source of vibration causing objectionable snoring noise. The structure of the present invention can be employed in all such orthoses and in other similar applications; however, the invention is described in particular relationship to a snore prevention device.

Several such snore prevention devices are commercially available both for use by dentists and consumers directly in which the consumers position the unformed snore prevention device in boiling water and subsequently insert it in their mouths with their lower jaw projected forward slightly to allow the softened filler material to set and shape the mouthpiece, including the holder and moldable material, in a tooth-conforming configuration. Typically, both the upper and lower teeth are imprinted in the material which, when hardened, forms a finished snore prevention device which can be used on a nightly basis. With existing snore prevention devices, the filler material, however, when displaced by the teeth during the molding process, overfills the holder and results in excess material which is uncomfortable to the wearer's gums. The excess material must be trimmed and smoothed to provide the wearer with a comfortable finished product.

Thus, although snore prevention devices are effective in preventing or reducing snoring in individuals, the molding of the snore prevention devices by individuals and, particularly by the consumers themselves, frequently results in a less than desirable fit for comfort or, if a dental care professional is fitting such a device, it requires additional work, thereby increasing the cost to the consumer. There exists a need, therefore, for an improved snore prevention device which can be molded by the consumer, which is relatively inexpensive, easy to use, provides a comfortable fit, and is effective in preventing snoring. To mold such devices, it is typically necessary to heat the thermoplastic material, such as by insertion into boiling water for a period of time, cooling the device slightly, and then inserting into the mouth while still in a plastic state to solidify and complete the process. The handle of this invention makes the immersion of a moldable device into boiling water safe and readily accomplished.

SUMMARY OF THE INVENTION

In a preferred embodiment of the invention, a handle includes an arm with an oral orthosis engaging member at one end. The engaging member includes one of a tab or slot which removably engages the oral orthosis. In a preferred embodiment, the arm further includes a hook-like member for supporting the oral orthosis on the rim of a container of boiling water during the molding process. In one embodiment, the arm forms a cover for a storage case for the orthosis.

Thus, with the present invention, an improved orthosis is provided in combination with a handle that facilitates molding of the device. This results in a moldable orthosis which can be easily molded by a consumer to provide a comfortable and effective device to reduce or eliminate snoring.

These and other features, objects and advantages of the present invention will become apparent upon reading the following description thereof together with reference to the accompanying drawings.

DETAILED DESCRIPTION OF THE PREFERRED EMBODIMENT

Figures 1, 2:
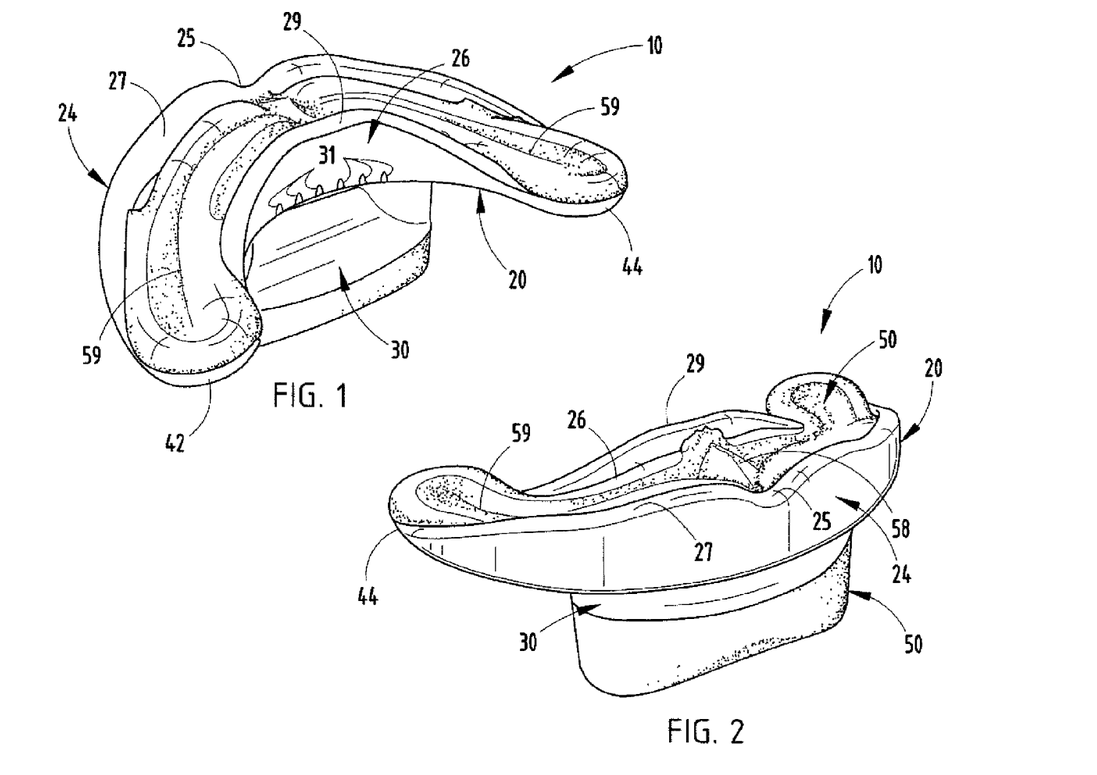
FIG. 1 is a rear perspective view of a snore prevention device embodying the present invention.
FIG. 2 is a front perspective view of the snore prevention device shown in FIG. 1.
Figure 3:
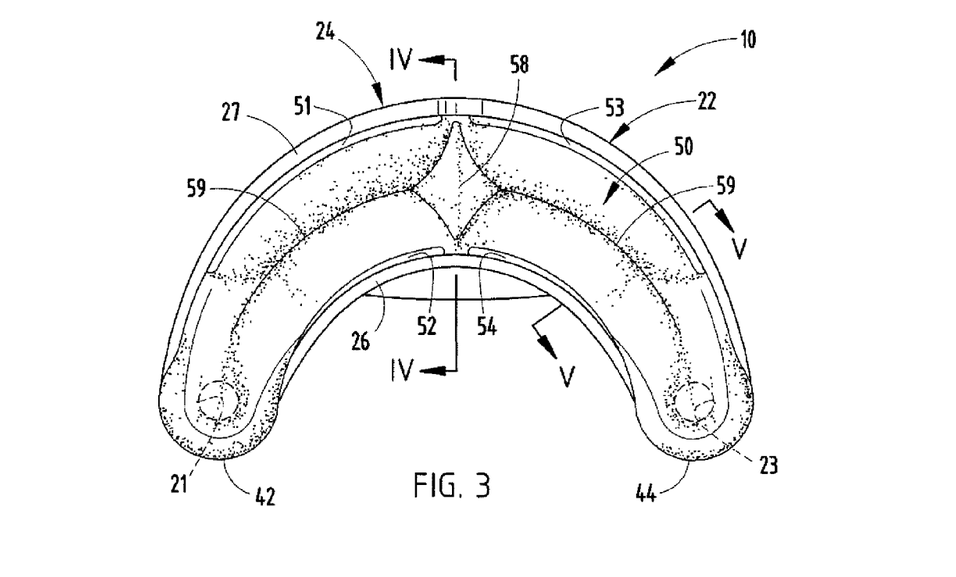
FIG. 3 is a top plan view of the snore prevention device shown in FIGS. 1 and 2.

Referring initially to FIGS. 1-3, there is shown a orthosis embodying the present invention. The invention can be employed for making a variety of different orthoses as noted above however, for purposes of illustration, an orthosis such as a snore prevention device 10 embodying the present invention is described as one preferred embodiment. The snore prevention device 10 comprises two basic elements including a semi-rigid outer member or holder 20 and a formable filler material 50 within the holder. The holder 20 is generally in the shape of a mouthpiece and includes an arcuate trough 22 (FIGS. 4-5) at an upper section thereof. The trough is defined by a front arcuate wall 24, a rear arcuate wall 26 spaced from said front wall, and a floor 28 (FIGS. 4 and 5) integrally joining the walls. Holder 20 also includes a downwardly projecting pedestal 30 integrally molded to the floor and coupled to the outer lower surface 29 (FIG. 6) of floor 28 by a pair of integral spaced-apart legs 32 and 34 defining an air transmission or breathing slot 40 between the lower surface 29 of trough floor 28 and the upper surface 35 of pedestal 30. Slot 40 extends through the snore prevention device 10 to provide a passageway for air between the lips of the user when the snore prevention device is in place. Slot 40 also facilitates coupling the device to a handle 60 (FIGS. 8-10) during the molding process, as described below.

Figure 4:
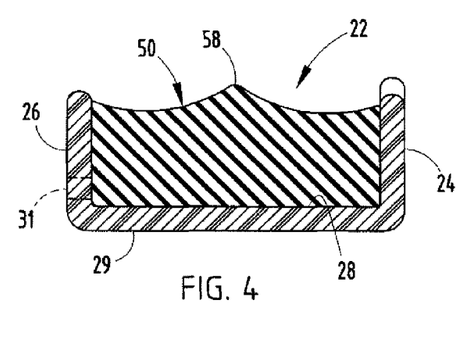
FIG. 4 is an enlarged cross-sectional view of the snore prevention device take along section line IV-IV in FIG. 3.
Figure 5:
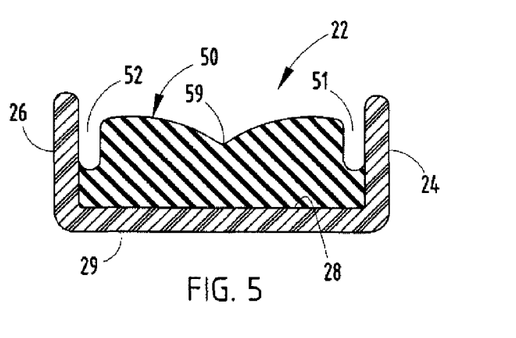
FIG. 5 is an enlarged cross-sectional view of the snore prevention device taken through section line V-V of FIG. 3.

The holder 20 is typically made of a resilient, semi-rigid polymeric material, such as polycarbonate or methylmethacrylate, although the thermoplastic resin preferred is polycarbonate made by the General Electric Company and sold under the trademark Lexan®. The three-dimensional shape of the holder 20 is molded in a conventional injection molding machine such that trough 22 of holder 20 is generally semicircular (as viewed from the top view of FIG. 3) and has a generally U-shaped cross section, as seen in FIGS. 4 and 5. The front wall 24 of the trough 22 is curvilinear and generally lip-shaped (i.e. generally higher toward the middle and shorter at the outer edges). Wall 24 has a concave indentation 25 at the center for assisting in centering the mouthpiece in alignment with the front teeth of a person's mouth during the molding process described below. The curvilinear top edge 27 of wall 24 curves downwardly toward the ends 42 and 44, which are substantially flat, and integrally join with the rear wall 26, which extends upwardly toward the center and is flattened at plateau 29, which is slightly lower than the indentation 25 in the front wall 24. The holder includes air escape apertures, and, in one embodiment, they are formed in the rear wall 26 which includes a plurality of apertures 31 (FIG. 1) which allow air to escape the trough 22 as teeth displace the formable material during the molding process described below.

Figure 6:
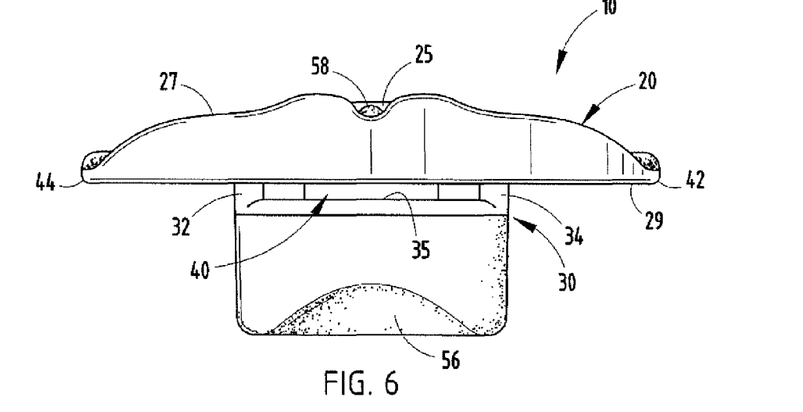
FIG. 6 is a front elevational view of the snore prevention device shown in FIGS. 1-3.
Figure 7:
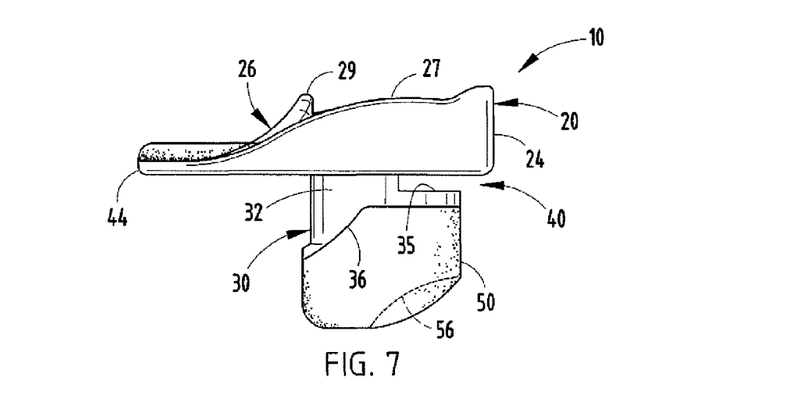
FIG. 7 is a right side elevational view of the snore prevention device shown in FIG. 6.

The formable or moldable material 50 which is positioned in the holder 20 for molding to the shape of the user's mouth and teeth preferably comprises an ethylene vinyl acetate copolymer resin. This material, or its equivalent, has a softening and molding temperature of between about 125° F.-175° F. and preferably about 150° F. Such material is sold by the E. I. DuPont de Nemours & Company under the trademark Elvax®. The material 50 is injection molded in a second molding step in which the holder 20 is positioned within a mold and the material 50, in the shape shown in FIGS. 1-7, is injection molded to partially fill the trough 22. The filler material is smaller than the trough 22, leaving voids 51 and 53 near the front wall 24 as best seen in FIG. 3, and voids 52 and 54 in the edges adjacent rear wall 26. This leaves, as also seen in FIG. 5, voids which allow the material 50 to flow into the trough 22 without overfilling and leaving excess material over the edges of the holder 20. Pedestal 30 likewise has formable material 50 injection molded in a curved pattern having a concavity 56, as best seen in FIGS. 6 and 7, and a ramp 36 to generally urge the lower jaw forwardly as the consumer forms the formable material 50 in his or her jaw between upper and lower teeth. Material 50, at the interface with pedestal 30, follows the inclined ramp 36 of pedestal 30, as best seen in FIG. 7. The concavity 56 likewise represents a void into which the material 50 can be displaced during the fitting process, further reducing trimming.

The material 50 in the upper trough 22 includes a raised curvilinear indexing land 58 to provide a guide for centering the device in conjunction with the indentation 25 located between the front teeth when placed in the user's mouth. The moldable insert material 50 also includes an arcuate alignment trough 59 on either side of the center land 58 which extends in an arcuate curve toward ends 42 and 44 for also assisting in centering the edges (i.e. biting surfaces) of the upper teeth within the holder 20 in alignment with the moldable filler material 50

In one embodiment of the invention, the arcuate length of the holder 20 along the outer wall 24 was about 3¼ inches and circumscribed and arc of approximately 180° and was substantially semicircular. The inner wall had an overall arc length of about 2¼ inches while the maximum depth of the trough 22 was approximately ¼ inch. Voids 51-54 have a gap width of approximately from about 0.030 to about 0.070 inches and in one embodiment were 0.040 inches. The voids have a depth of from about 0.030 inches to about 0.190 inches and in one embodiment had a depth of approximately 0.190 inches at the deepest section near the crown in wall 24 adjacent notch 25. The arc length for the front pair of voids 51, 53 are about 0.70 inches each and the rear pair 52, 54 are about 0.40 inches each. It is important that the sum of the volume of the voids are close to the average sum of the volume of the average teeth that will form the impressions. That can be accomplished by varying the proportions and/or number of voids. The limiting factor to any configuration is that the teeth should be adequately surrounded after forming to maintain the proper position of the orthosis.

Breathing slot 40 is sized to provide sufficient air for comfortable breathing and is tapered from front to back. In one embodiment it had an opening at the front of about 0.75 inches when viewed from FIG. 6 and is tapered rearwardly to an opening of approximately 0.06 inches at the rear of the slot. Its height (in one embodiment) was approximately 0.1 inch. These dimensions of the mouthpiece can be varied, although the dimensions given are for a snore prevention device which will comfortably fit most averaged sized mouths. The molded insert material 50 naturally adheres to holder 22; however, the floor 28 of holder 22 includes two circular apertures 21 and 23, as seen in FIG. 3, for receiving material 50 for locking it securely in place.

In order to mold the orthosis shown in FIGS. 1-7, it is held by a suitable handle 60 in a vessel 80 (FIG. 10) of boiling water 82 for a period of time such that the formable material becomes softened. Since material 50 has a significantly lower softening temperature than that of the polycarbonate holder 20, immersion of the device in a heated fluid, such as boiling water, prior to fitting softens the material 50 to accept the user's tooth pattern.

Figures 8, 9, 10, 11, 12:
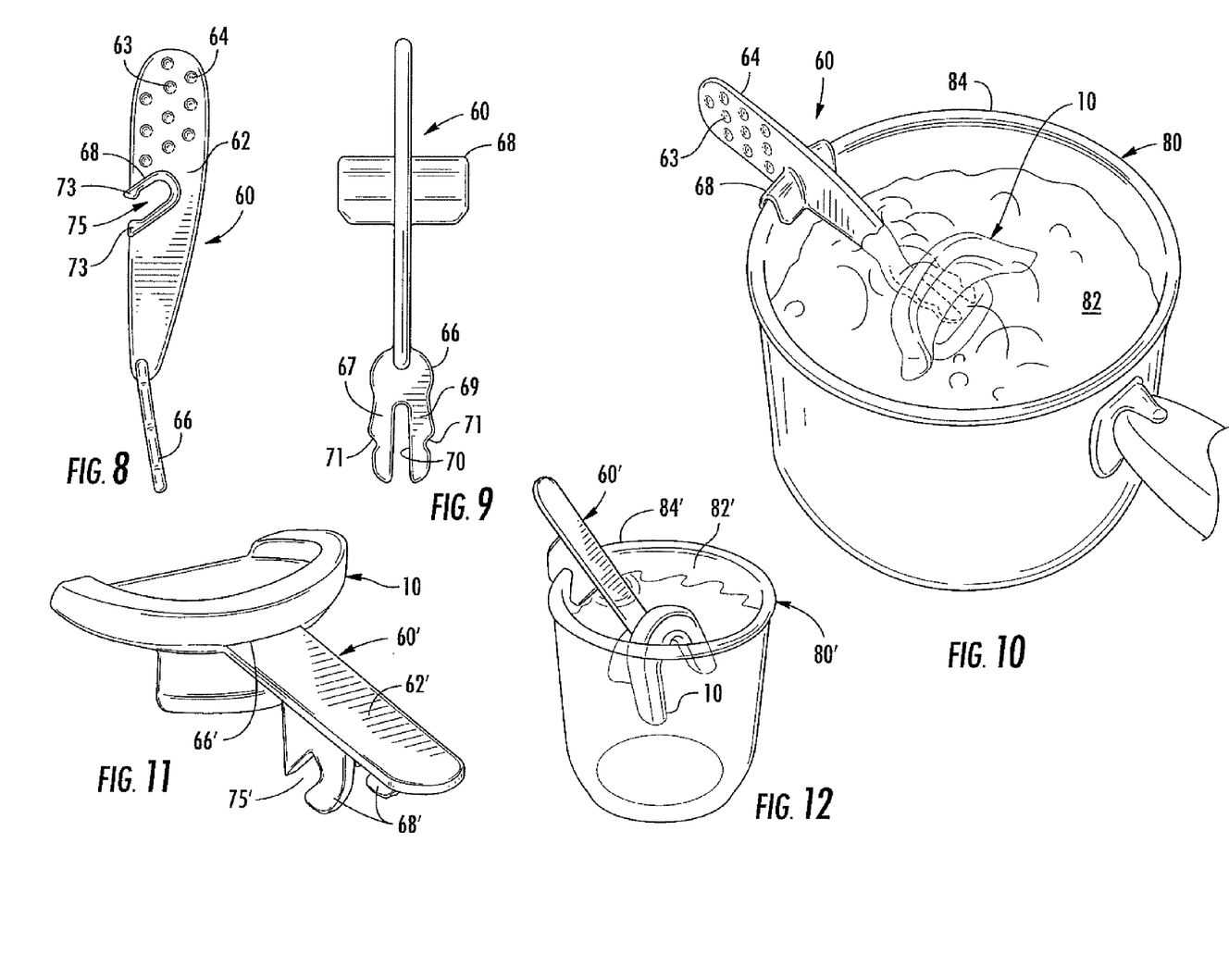
FIG. 8 is a right side elevational view of a handle embodying the present invention.
FIG. 9 is a front elevational view of the handle shown in FIG. 8.
FIG. 10 is a perspective view of the handle shown in use holding an oral orthosis in a pan of boiling water.
FIG. 11 is a perspective view of an alternative embodiment of the handle, shown coupled to an oral orthosis.
FIG. 12 is a perspective view of the embodiment shown in FIG. 10, shown mounted to a container for boiling water.

FIGS. 8-22 show a variety of handles employed for safely holding the oral orthosis device 10 in boiling water during the molding process. In each of the embodiments, the handle, such as handle 60 in FIGS. 8-10, clips onto the oral orthosis 10, typically by insertion of an engaging end into slot 40. In FIGS. 8-10, one design of a handle 60 is shown and includes an elongated arm 62 having a gripping member 64 at one end and an engaging member 66 at its opposite end for engaging the orthosis 10. In a preferred embodiment of the invention, the handle 60 includes a slot or hook-like member 68 intermediate gripping member 64 and engaging member 66 to allow it to be held on the rim 84 of a vessel 80, such as a pot, inclining the orthosis 10 in a submersed position with respect to the boiling water 82, as illustrated in FIG. 10. In a preferred embodiment of the invention, as shown in FIGS. 8-10, the gripping member 64 includes gripping projections 63 which facilitates holding of the handle 60 between the index finger and thumb of an individual using the device. The engaging member 66 comprises, as best seen in FIGS. 9 and 10, a fork-like tined extension of arm 62, which is integral with the arm and includes a pair of tines 67 and 69 with a slot 70 therebetween. The outer edges of tines 67 and 69 each include a notch 71 which engages the edges of slot 40 holding the orthosis 10 to the engaging member 66. For such purpose, times 67 and 69 compress into slot 70, such that a spring bias force is provided by notch 71 against the outer edges of slot 40 to securely hold the orthosis 10 to the handle 60. The hook-like member 68 includes a pair of inwardly extending projections 73 (FIG. 8) formed in an elongated, generally U-shaped body which is integral with arm 62 and is somewhat flexible to allow the slot 75 of member 68 to extend over the rim 84 of pot 80. The projections 73 securely hold the handle 62 and orthosis 10 coupled thereto to the edge of the pot, immersing the orthosis as shown in FIG. 10.

FIGS. 11 and 12 shown an alternative embodiment of handle 60', which includes an engaging member 66' of substantially the same construction as the previous embodiment and which fits within the slot 40 of orthosis 10. Handle 60' of FIGS. 11 and 12 includes a flat arm 62' and a pair of spaced-apart downwardly extending legs 68' having inclined slots 75' which grip the rim 84' of a container 80', such as a beaker filled with water 82'. Container 80' can be placed in a microwave oven for alternate heating of the water 82' to a boiling point. The handle 60' likewise holds the orthosis 10 immersed in boiling water during the molding process. Another alternative embodiment of a handle for holding the orthosis in a container of boiling water, shown in FIGS. 13-15.

Figure 13:
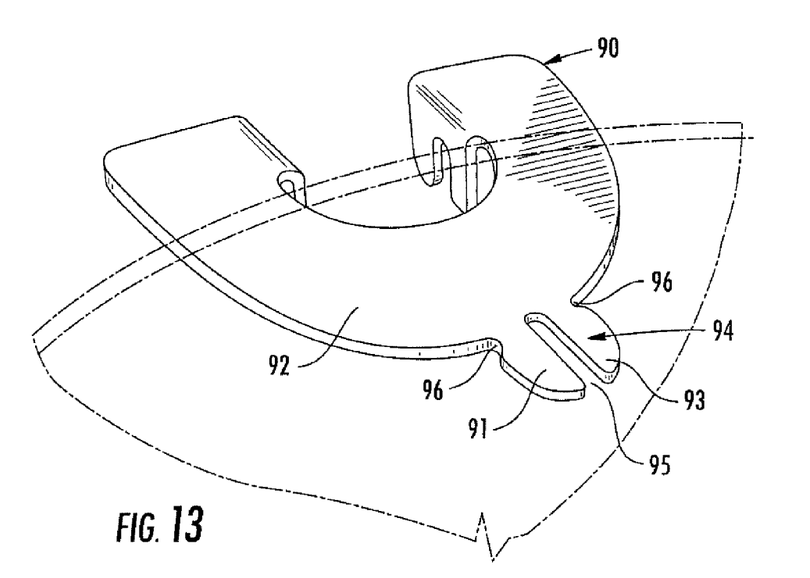
FIG. 13 is a perspective view of yet another embodiment of a handle embodying the present invention.
Figures 14, 15:
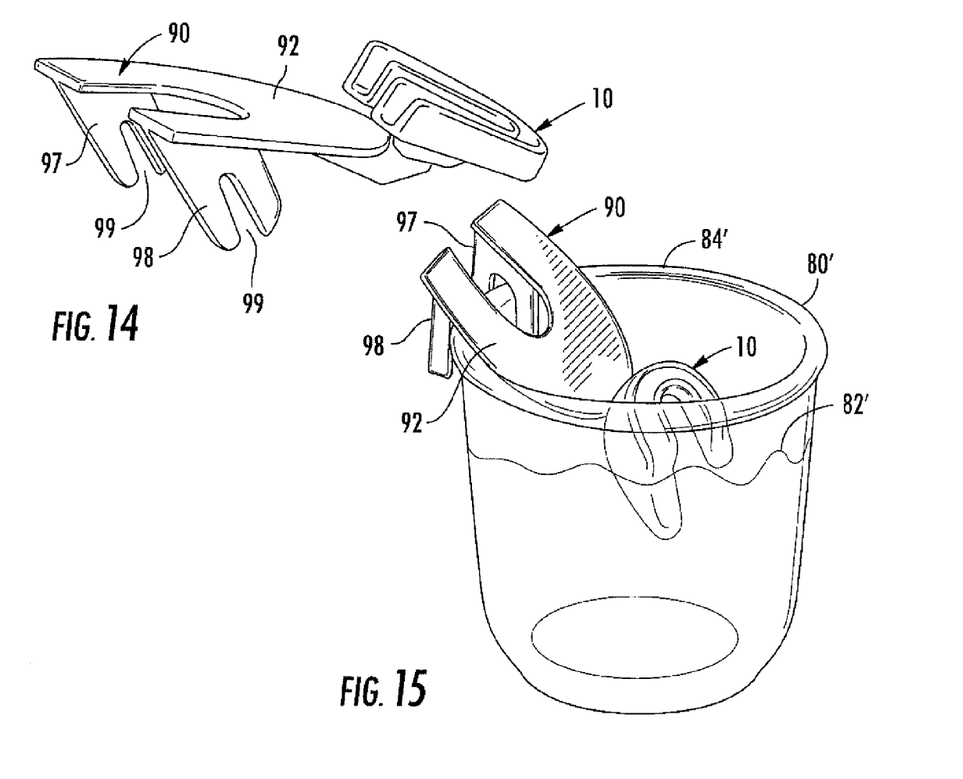
FIG. 14 is a right side perspective view of the handle shown in FIG. 13, shown coupled to an oral orthosis device.
FIG. 15 is a perspective view of the handle shown in FIGS. 13 and 14, shown in a position for immersing the oral orthosis in a container of heated water.

In FIGS. 13-15, a handle 90 is shown which includes a generally U-shaped body 92 having a tined engaging member 94 including tines 91 and 93 on opposite sides of a slot 95 extending outwardly from one end of body 92. Tines 91 and 93 compress and engage edges of slot 40 in the previously described orthosis 10 with indentations 96 at the junction of tines 91 and 93 and body 92 lockably but removably engaging opposite edges of slot 40. Handle 90 includes gripping member 97 and 98 extending downwardly from the under surface of body 92 at an end opposite engaging member 94. Each of the gripping members 97 and 98 provide a dual function of allowing the user to grip the handle 90, as well as place it over the edge 84' of a vessel 80', such as a beaker filled with water 82'. For such purpose, each of the gripping members 97, 98 include tapered slots 99, which accommodate different sized vessels 80' and are inclined at an acute angle to cant the orthosis 10 in vessel 80' below the surface of boiling water 82' which can be heated in vessel 80'.

Figure 16:
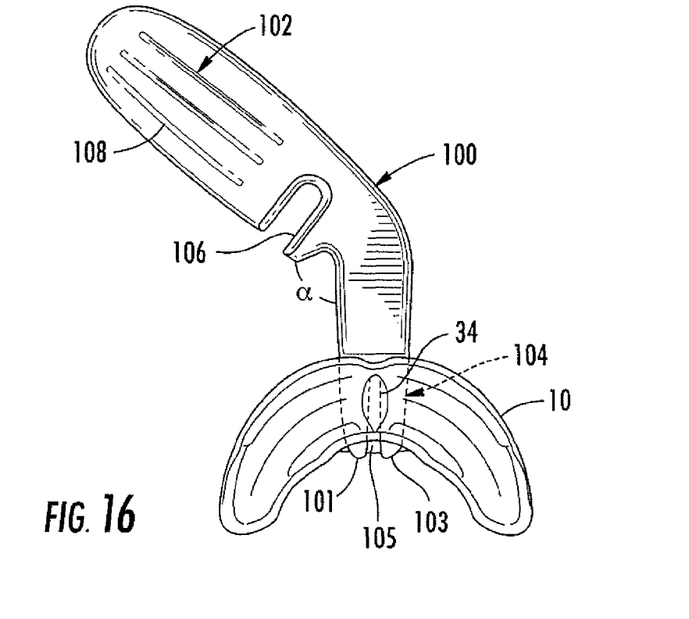
FIG. 16 is a right side elevational view of another alternative embodiment of the handle of the present invention.
Figure 17:
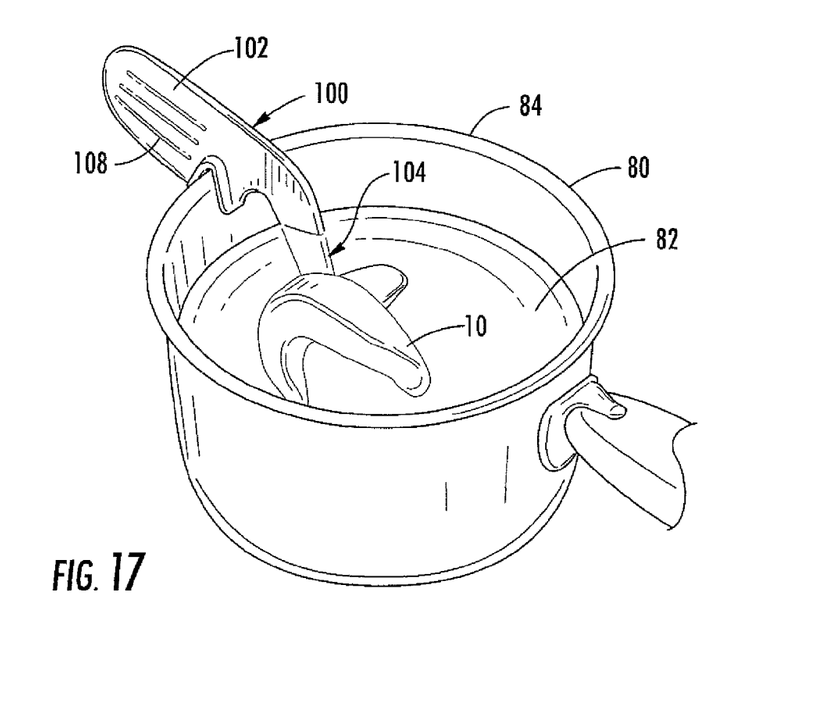
FIG. 17 is a perspective view of the handle shown in FIG. 16, shown coupled to a pan for heated water.

FIGS. 16 and 17 illustrate yet another embodiment of a handle 100 for holding an oral orthosis device 10 in a container, such as on the rim 84 of a pot 80, and submerging the orthosis 10 in boiling water 82. Handle 100 includes a gripping member 102 at one end and an engaging member 104 at its opposite end. Intermediate members 102, 104 is a hook 106 extending into the body of handle 100, which is formed at an acute angle α (FIG. 16) between members 102, 104 to position the orthosis 10 in a submerged position, as seen in FIG. 17. Member 104 includes a pair of tines 101, 103 on opposite sides of a slot 105, which extends over one of the legs 32 or 34 (FIG. 6) of the orthosis 10 instead of engaging the slot 40 of orthosis 10. Gripping member 102 includes projections 108 to facilitate gripping of the handle 100 during use.

Figure 18:
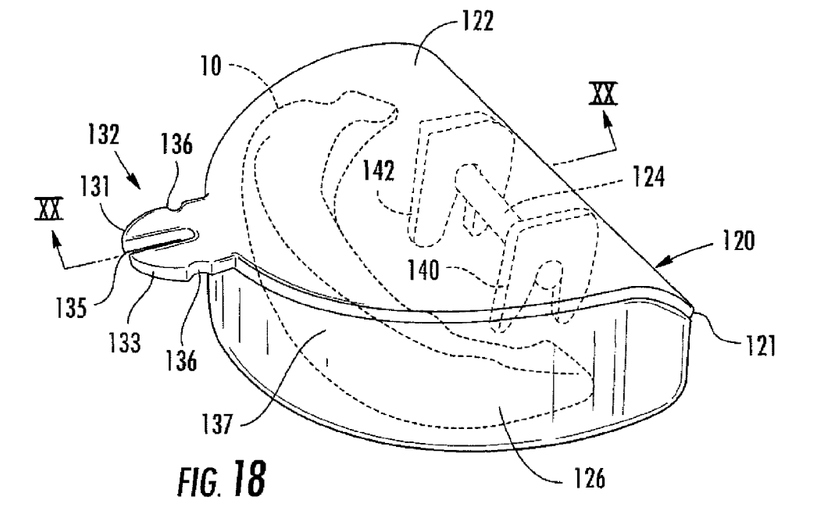
FIG. 18 is a container for an oral orthosis device which includes a hinged lid which forms a handle for immersion of the oral orthosis device in boiling water.
Figure 19:
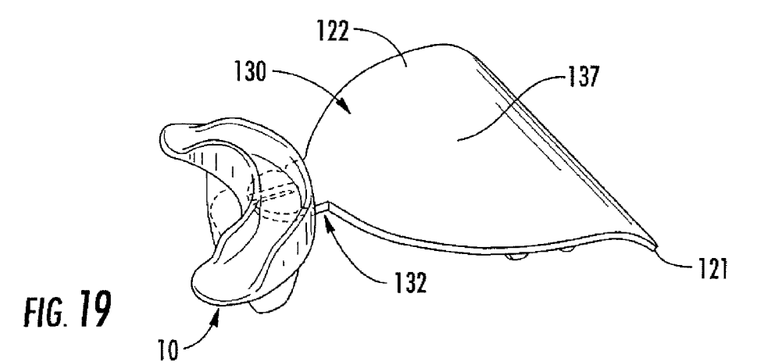
FIG. 19 is a perspective view of the lid removed from the container, shown coupled to an oral orthosis device.
Figure 20:
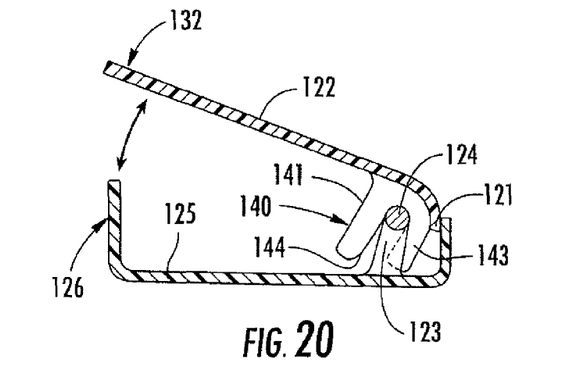
FIG. 20 is a cross-sectional view of the container shown in FIG. 18, taken along section lines XX-XX.

FIGS. 18-20 disclose a storage case 120 for holding an orthosis 10 when not in use. The cover 122 of case 120 is generally a semicircular planar member with a downwardly curved edge 121 opposite an orthosis engaging member 132. The cover 122 is pivotally mounted to an axle 124 extending upwardly from the floor 125 of bottom section 126 of case 120 by means of a pedestal 123. Cover 122 can be pivoted between a closed position, shown in FIG. 18, to an open position, shown in FIG. 20, and subsequently removed from the case 120 as illustrated in FIG. 19. In this position, it defines a handle 130 for holding the orthosis 10 for immersion in a container, such as shown in the earlier embodiments. Cover 122, which defines a handle 130 as shown in FIG. 19, once removed from the bottom 126 of the storage case 120, includes an engaging member 132 which is similar to the engaging member in prior embodiments, namely, a forked member having tines 131, 133 with a slot 135 therebetween for insertion into the slot 40 of orthosis 10 (FIG. 18). The tines include notches 136 near the junction of engaging member 132 and the body 137 of handle 130. Handle 130 is pivotally coupled to pivot axle 124 by means of the hook-like members 140 and 142, each of which define a hook for fitting over the edge of a pot or beaker, as shown in the prior embodiments. For such purpose, each of the hooks 140, 142 includes legs 141 and 143 having a tapered slot 144 (FIG. 20) therebetween which fits over the edge of a container holding boiling water, as in the embodiments of FIGS. 13-15, with slots 144 and hooks 140, 142 canted at an angle such that the orthosis held by engaging member 132 will extend downwardly at an angle into the boiling water.

Figure 21:
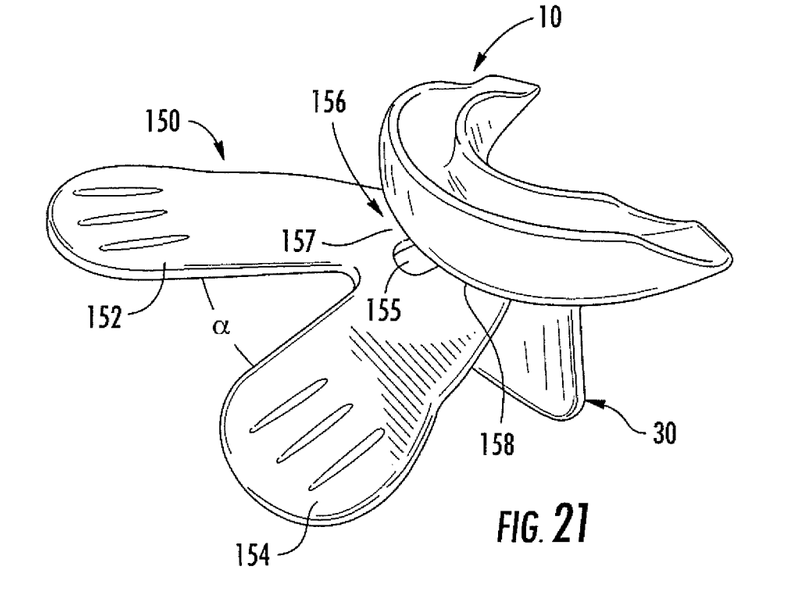
FIG. 21 is a perspective view of yet another alternative embodiment of the handle embodying the present invention, shown coupled to an oral orthosis.
Figure 22:
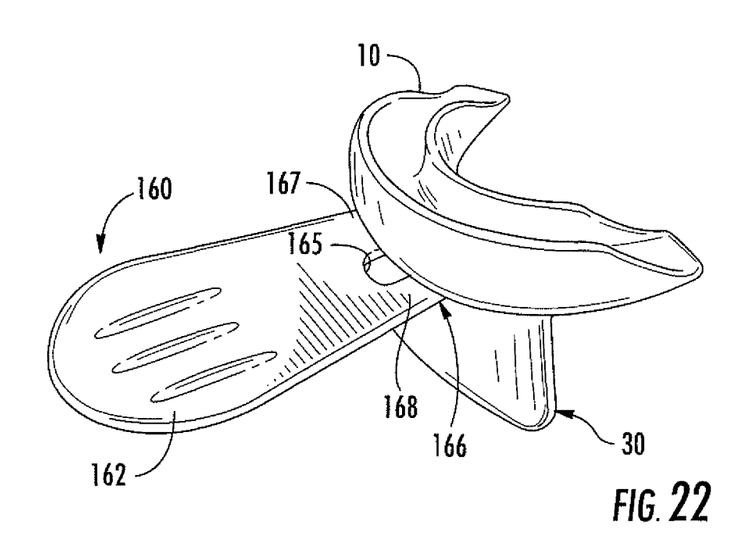
FIG. 22 is yet further embodiment of a handle embodying the present invention.

FIGS. 21 and 22 show yet other embodiments of the invention. In FIG. 21, a handle 150 is provided and has two paddle-like layered planar arms 152 and 154 extending convergingly at an acute angle α to an engaging member 156. Engaging member 156 is of construction similar to the remaining engaging members, namely, a pair of tines 157 and 158 with a slot 155 therebetween such that the tines snap-fit within the aperture 40 in orthosis 10, as illustrated in FIG. 21. FIG. 22 shows a similar handle 160 with a single tapered arm 162 and tines 167, 168 at an opposite end with a slot 165 therebetween. The engaging member 166 so-defined fits within the slot 40 of the orthosis 10. In the embodiments shown in FIGS. 21 and 22, the junction of handles 150 and 160 to the pedestal 30 of the orthosis 10, forms the hook for holding and tilting the orthosis into a container of boiling water. With each of the handle embodiments shown in FIGS. 8-22, therefore, a conveniently used handle is provided for immersing the orthosis in boiling water during the molding process for plasticizing the filler material for subsequent molding. Each of the handles of FIGS. 8-22 are integrally molded of a suitable polymeric material, such as polycarbonate.

The custom fitting of the orthosis is accomplished by removing the snore prevention device 10 from the boiling water using one of the handles, such as handle 60, allowing it to cool for a short period of time, and inserting the device into the user's mouth with the notch 25 (FIGS. 1 and 2), indexing land 58, and alignment trough 59 (FIGS. 1-3) guiding the positioning of the device into one's mouth. The tapered concavely curved edge 56 engages the inside of the lower teeth and tends to move the jaw slightly forwardly during the molding process. The user need only grip the snore prevention device between his/her teeth for 30 seconds or so to allow the thermoplastic filler 50 to set in a comfortable, upper and lower teeth engaging configuration, whereupon the device can be removed. It then contains a permanent imprint of the user's upper and lower teeth in which the lower teeth engage edge 56 of the pedestal to urge the lower jaw slightly forwardly an amount of typically from about 2 mm to about 6 mm, sufficient to provide clearance between the back of the tongue and uvula to prevent or greatly reduce snoring during sleep.

The durable material is employed for the snore prevention device 10 to hold its shape and be useful for a significant amount of time and can be periodically sanitized as desired by the user and stored when not in use. Although the dimensions given are for medium sized snore prevention devices, it should be understood that the dimensions can be proportionally varied to make larger or smaller snore prevention devices as desired. The provision of the self-alignment guides, as well as the voids and air escape apertures or vents, provides an orthosis which, upon impressing the tooth pattern, does not result in an excess amount of material which must be trimmed for comfort and allows immediate use without such a step. The formable material 50 and/or the holder 20 can be colored to color code the snore prevention device for an individual user.

It will become apparent to those skilled in the art that various modifications to the preferred embodiment of the invention as described herein can be made without departing from the spirit or scope of the invention as defined by the appended claims.

The invention claimed is:

1. A handle serving as a removable cover for a storage case for a moldable orthosis, said handle employed for positioning an orthosis in a container of molding solution, said handle comprising:

a semicircular body having one end which is substantially straight and an orthosis engaging member along an edge opposite said one end wherein said engaging member comprises a pair of spaced-apart tines for insertion into a slot of the orthosis for coupling the handle to the orthosis; and a pair of spaced-apart legs extending downwardly from said body near said one end, said legs each having a slot formed therein to provide a removable coupling to an axle of the storage case allowing the opening and closing of the cover and also serving to engage a rim of a container of molding solution to position an orthosis coupled to said engaging member in a submerged position in the container.

2. The handle as defined in claim 1 wherein said one end of said body is downwardly curved.

3. The handle as defined in claim 1 wherein said tines include notches for engaging edges of a slot in an orthosis.

* * * * *